United States Patent
Sawai et al.

(10) Patent No.: US 9,372,187 B2
(45) Date of Patent: *Jun. 21, 2016

(54) DETECTION METHOD AND DETERMINATION METHOD FOR DETECTION TARGET

(75) Inventors: Toshiya Sawai, Chiba (JP); Eri Oowada, Saitama (JP); Yasunobu Sato, Chiba (JP); Hirokazu Nagaoka, Chiba (JP); Satoru Sugita, Chiba (JP)

(73) Assignees: ORTHO-CLINICAL DIAGNOSTICS KABUSHIKI KAISHA (JP); JNC CORPORATION (JP)

( * ) Notice: Subject to any disclaimer, the term of this patent is extended or adjusted under 35 U.S.C. 154(b) by 1306 days.

This patent is subject to a terminal disclaimer.

(21) Appl. No.: 12/810,038

(22) PCT Filed: Dec. 25, 2008

(86) PCT No.: PCT/JP2008/073625
§ 371 (c)(1),
(2), (4) Date: Sep. 13, 2010

(87) PCT Pub. No.: WO2009/084595
PCT Pub. Date: Jul. 9, 2009

(65) Prior Publication Data
US 2011/0014713 A1 Jan. 20, 2011

(30) Foreign Application Priority Data

Dec. 28, 2007 (JP) ................. 2007-339990

(51) Int. Cl.
*G01N 33/533* (2006.01)
*G01N 33/543* (2006.01)

(52) U.S. Cl.
CPC .... *G01N 33/54333* (2013.01); *G01N 33/54306* (2013.01)

(58) Field of Classification Search
CPC ................... G01N 33/54306; G01N 33/54333
USPC .......................................................... 436/526
See application file for complete search history.

(56) References Cited

U.S. PATENT DOCUMENTS

| 5,998,588 A | 12/1999 | Hoffman et al. |
| 2003/0165962 A1 | 9/2003 | Furukawa et al. |

(Continued)

FOREIGN PATENT DOCUMENTS

| CA | 2 656 203 A1 | 1/2008 |
| EP | 2 037 272 A1 | 3/2009 |

(Continued)

OTHER PUBLICATIONS

Jayagopal, Ashworth et al., "Surface Engineering of Quantum Dots for In Vitro Vascular Imaging", Bioconjugate Chem., vol. 18, 2007, pp. 1424-1433.

(Continued)

*Primary Examiner* — Mark Shibuya
*Assistant Examiner* — Pensee Do
(74) *Attorney, Agent, or Firm* — Cantor Colburn LLP

(57) ABSTRACT

A detection/determination kit with which a substance to be detected or the amount thereof can be rapidly, inexpensively, and easily detected or determined; and a detection/determination method. The kit, which is for detecting a substance to be detected (50) contained in a specimen, comprises: a first compound (10) comprising a first substance including a stimulus-responsive polymer (11) and, bonded to the first substance, a first antibody (13) against the substance (50); and a second compound (20) comprising a second substance (21) which is hydrophilic and, bonded thereto, a second antibody (23) against the substance (50). The first antibody (13) and second antibody (23) can simultaneously combine with the substance (50) at different sites in the substance (50).

4 Claims, 8 Drawing Sheets

(56) References Cited

U.S. PATENT DOCUMENTS

| | | | |
|---|---|---|---|
| 2004/0126899 A1* | 7/2004 | Lee et al. | 436/518 |
| 2005/0113297 A1* | 5/2005 | Francois et al. | 514/12 |
| 2006/0194887 A1 | 8/2006 | Kojima et al. | |
| 2010/0081204 A1 | 4/2010 | Miyata et al. | |

FOREIGN PATENT DOCUMENTS

| | | | |
|---|---|---|---|
| JP | 58-11575 B2 | 3/1983 | |
| JP | 2869684 B2 | 3/1999 | |
| JP | 2927601 B2 | 7/1999 | |
| JP | 2002-85957 A | 3/2002 | |
| JP | 2005082538 A | 3/2005 | |
| JP | 3693979 B2 | 7/2005 | |
| JP | 2006242597 A | 9/2006 | |
| JP | 3845249 B2 | 11/2006 | |
| JP | 2007071832 A | 3/2007 | |
| JP | 3916330 B2 | 5/2007 | |
| JP | 2007244374 A | 9/2007 | |
| JP | 4071738 B2 | 4/2008 | |
| WO | WO 97/09068 A1 | 3/1997 | |
| WO | 01/09141 A1 | 2/2001 | |

OTHER PUBLICATIONS

Notice of Reasons for Rejection issued to Canadian Application No. 2,710,586, mailed Oct. 23, 2012.

Office Action issued to Chinese Application No. 200880123629.8, dated Nov. 29, 2012 (includes English translations of Office Action, Notice of Reasons for Rejection, and Search Report).

Final Office Action issued to U.S. Appl. No. 12/306,178, mailed Dec. 6, 2011.

Office Action issued to U.S. Appl. No. 12/306,178, mailed Apr. 22, 2011.

Furukawa et al., Affinity selection of target cells from cell surface displayed libraries: a novel procedure using thermoresponsive magnetic nanoparticles, 2003, Appl. Microbiol. Biotechnolog., 62, 478-483.

Data sheet ZZ domain, downloaded from the Internet [URL:http://www.ncbi.nlm.nih.gov/protein/2SPZ_A], printed on Apr. 9, 2011, p. 1.

Hoffman, A. S., et al, "Founder's Award, Sixth World Biomaterials Congress 2000, Kamuela, HI, May 15-20, 2000; Really smart bioconjugates of smart polymers and receptor proteins", J. Biomed. Mater. Res., vol. 52, No. 4, Dec. 15, 2000, pp. 577-586.

Supplementary European Search Report for EP 08 86 6922.1, dated May 25, 2011.

Office Action issued to European Patent Application No. 08866922.1, mailed Feb. 20, 2012.

Chen et al., "Temperature-Responsive Magnetite/PEO-PPO-PEO Block Copolymer Nanoparticles for for Controlled Drug Targeting Delivery", Langmuir: The ACS Journal of Surfaces and Colloids, vol. 23, No. 25, Dec. 4, 2007, pp. 12669-12676, XP002609574.

Non-Final Action issued to U.S. Appl. No. 12/810,454, mailed Jun. 5, 2014.

* cited by examiner

DETECTION METHOD AND DETERMINATION METHOD FOR DETECTION TARGET

CROSS-REFERENCE TO RELATED APPLICATIONS

This application is a National Stage of International Application No. PCT/JP2008/073625, filed Dec. 25, 2008, which claims the benefit of Japanese Application No. 2007-339990, filed Dec. 28, 2007, the contents of which is incorporated by reference herein.

FIELD OF THE INVENTION

The latex aggregation method has long been used for detecting a target substance in a sample. In the latex aggregation method, in order to detect an antigen present in liquid such as a biological sample, the liquid and latex carrying an antibody or a fragment thereof that specifically binds to the target antigen are mixed, and the degree of latex aggregation is measured to detect or quantify the antigen (e.g., Japanese Published Examined Patent Application No. S58-11575, hereinafter referred to as Patent Document 1).

BACKGROUND OF THE INVENTION

According to the latex aggregation method, aggregation of latex is facilitated by an antigen, which is added as a sample and cross-links a plurality of latex-bound antibodies. This simple procedure allows for easy and rapid detection of an antigen. However, when the amount of the antigen is small, since it is difficult to generate cross-linking, a sufficient amount of latex cannot aggregate. Therefore, it has been difficult to detect a small amount of antigen. In addition, in manual measurement, there has been a problem in measured results which show large variations.

Thus, methods utilizing an enzyme-substrate reaction, such as ELISA and CLEIA, are widely adopted. In these methods, for example, a primary antibody that binds specifically to an antigen is bound to an antigen, and a secondary antibody having an enzyme is bound to this primary antibody. Then, an enzyme substrate is added and the reactivity of a reaction catalyzed by the enzyme is measured to detect or quantify an antigen.

According to these methods, by using a luminescent reagent as a substrate, for example, the high detectability of a luminous reaction after adding the substrate allows detection of a small amount of antigen.

SUMMARY OF THE INVENTION

Problems to be Solved by the Invention

However, the methods utilizing an enzyme-substrate reaction require special reagents and instruments such as a secondary antibody, luminescent reagent and photodetector, which make the operating cost high.

Moreover, as shown in FIG. 8, these methods consist of a plurality of steps that make the operation complex, such as incubation of the specimen and each reagent (ST110 and ST130), cleaning of the system (ST120), and detection of the luminous reaction (ST140). Each of these steps takes considerable time, and therefore these methods are not suitable for large-scale processing.

The present invention was developed in view of the above-mentioned situation. An object of the present invention is to provide a kit for detecting and/or quantifying a target substance that allows for rapid, inexpensive, and convenient detection and/or quantification of a target substance, and a method allowing for high-precision detection and/or quantification.

Means for Solving the Problems

The inventors found that the aggregation of the stimuli-responsive polymer is inhibited when a hydrophilic compound is brought into close proximity, to accomplish the present invention. Specifically, the present invention provides the following.

In a first aspect of the present invention, a kit for detecting and/or quantifying a target substance is provided, including:
a first bound substance in which a first substance including a stimuli-responsive polymer binds to a first affinity substance having affinity to the target substance; and
a second bound substance in which a hydrophilic second substance binds to a second affinity substance having affinity to the target substance, in which
the first affinity substance and the second affinity substance can bind simultaneously to different sites of the target substance.

In a second aspect of the present invention, the kit according to the first aspect is provided, in which the first substance contains a particulate magnetic material.

In a third aspect of the present invention, the kit according to the first or second aspect is provided, in which the second substance is a hydrophilic polymer.

In a fourth aspect of the present invention, the kit according to any one of the first to third aspects is provided, in which the second substance is a polyol.

In a fifth aspect of the present invention, the kit according to any one of the first to third aspects is provided, in which the second substance is a polymer containing polyoxyalkylene as a constitutional unit.

In a sixth aspect of the present invention, a method for detecting a target substance in a sample is provided, including steps of:
mixing a first bound substance in which a first substance containing stimuli-responsive polymer binds to a first affinity substance having affinity to the target substance, a second bound substance in which a hydrophilic second substance binds to a second affinity substance having affinity to the target substance, and the sample; placing the mixture under conditions to aggregate the stimuli-responsive polymer; and determining if the stimuli-responsive polymer is dispersed or not, in which
the first affinity substance and the second affinity substance can simultaneously bind to different sites of the target substance.

In a seventh aspect of the present invention, the method according to the sixth aspect is provided, in which the first substance contains a particulate magnetic material, and the method further includes a step of separating the aggregated magnetic material by applying a magnetic force.

In an eighth aspect of the present invention, a method for quantifying a target substance in a sample is provided, including steps of:
mixing a first bound substance in which a first substance containing a stimuli-responsive polymer binds to a first affinity substance having affinity to the target substance, a second bound substance in which a second substance, being hydrophilic, binds to a second affinity substance having affinity to the target substance, and the sample;

placing the mixture under predetermined conditions to aggregate the stimuli-responsive polymer;

calculating the amount of a target substance in the sample based on a correlation equation between the amount of the target substance and the turbidity under the predetermined condition.

In a ninth aspect of the present invention, the method according to the eighth aspect is provided, in which the first substance contains a particulate magnetic material, and the method further includes a step of separating the aggregated magnetic material by applying a magnetic force.

Effects of the Invention

According to the present invention, if a target substance is present, a first affinity substance and a second affinity substance bind to the target substance. Therefore, a stimuli-responsive polymer bound to the first affinity substance and a second substance bound to the second affinity substance are brought close to each other. Thus, a hydrophilic moiety is arranged in the vicinities of the stimuli-responsive polymer. Therefore, aggregation of the stimuli-responsive polymer responding to stimulus is inhibited. Therefore, by observing the inhibition of aggregation, the presence or absence of the target substance can be detected. In addition, by measuring the degree of the inhibition of aggregation, the target substance can be quantified.

All of the abovementioned procedures can be conducted without particularly using any special reagent or instrument, and therefore are inexpensive and convenient. Additionally, the abovementioned procedure only measures the degree of inhibition of aggregation and is not a system that utilizes a reaction catalyzed by an enzyme, and therefore can be conducted quickly. Furthermore, since the hydrophilic moiety of the second substance greatly inhibits the aggregation of the stimuli-responsive polymer, high-sensitivity detection and quantification of the target substance become possible.

EXPLANATION OF REFERENCE NUMERALS

Figure 1:
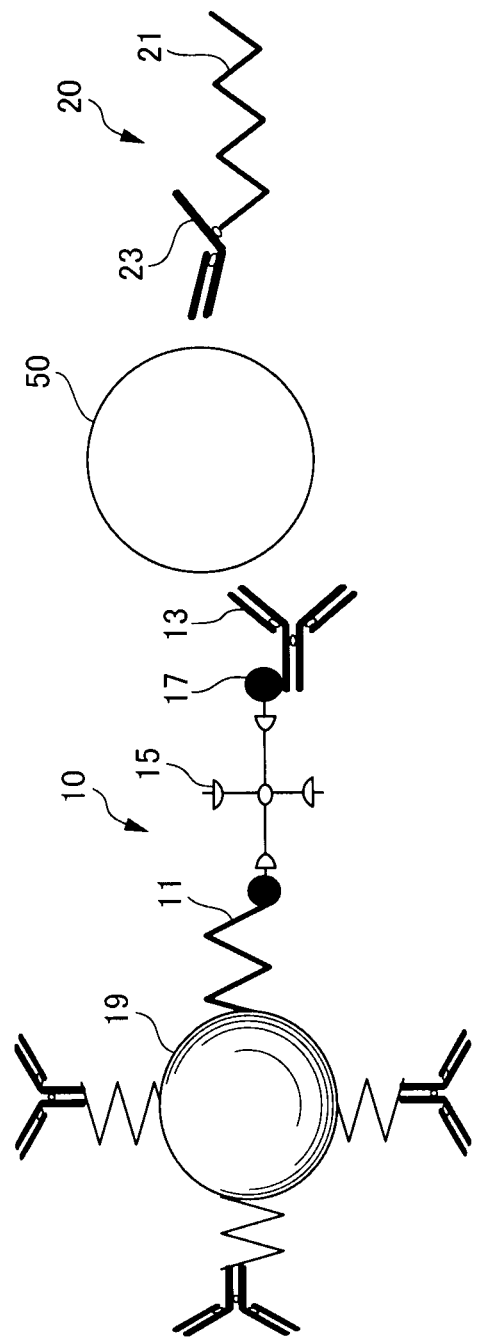
FIG. 1 is a schematic configuration diagram of the bound substance used in a method according to an embodiment of the present invention.

10 First bound substance
11 Stimuli-responsive polymer
13 First antibody (first affinity substance)
15 Avidin
17 Biotin
19 Magnetic material
20 Second bound substance
21 Second substance
23 Second antibody (second affinity substance)
50 Target substance
71 Cell
73 Permanent magnet

DETAILED DESCRIPTION OF THE PREFERRED EMBODIMENTS

Below, an example of the present invention is explained with reference to diagrams.

Kit

The kit of the present invention is a kit for detecting or quantifying a target substance including a first bound substance and a second bound substance. Next, each item is explained in detail.

First Bound Substance

The first bound substance is a substance in which a first substance containing a stimuli-responsive polymer binds to a first affinity substance having affinity to the target substance.

First Substance

The first substance used in the present invention contains a stimuli-responsive polymer which undergoes a conformation change in response to an external stimulus, thereby being a polymer that can adjust the aggregation and dispersion. The stimulus includes temperature change, irradiation of light, addition of acid or base (pH change), electric field change and the like, though not limited thereto.

Particularly, in the present invention, a temperature-responsive polymer which is able to aggregate and disperse by temperature change is preferred as a stimuli-responsive polymer. The temperature-responsive polymer includes polymers which have a lower critical solution temperature (hereinafter referred to as LCST), and polymers which have an upper critical solution temperature (hereinafter referred to as UCST).

Polymers used in the present invention which have lower critical solution temperatures, include: polymers having N-substituted (meth)acrylamide derivative such as N-n-propyl acrylamide, N-isopropyl acrylamide, N-ethyl acrylamide, N,N-dimethyl acrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine and N-methacryloyl morpholine; polyoxyethylene alkyl amine derivatives such as hydroxypropyl cellulose, polyvinyl alcohol partial acetal, polyvinylmethyl ether, (polyoxyethylene-polyoxypropylene) block copolymer, and polyoxyethylenelauryl amine; polyoxyethylenesorbitan ester derivatives such as polyoxyethylenesorbitanlaurate; (polyoxyethylenealkylphenyl ether) (meth)acrylates such as (polyoxyethylene nonylphenylether) acrylate, (polyoxyethyleneoctylphenylether)methacrylate; and polyoxyethylene(meth)acrylic ester derivatives such as (polyoxyethylene alkyl ether)(meth)acrylate of (polyoxyethylenelauryl ether)acrylate, (polyoxyethyleneoleyl ether) methacrylate. Furthermore, these polymers and copolymers having at least two unlike monomers of the above species can be used as well. In addition, a copolymer of N-isopropyl acrylamide and N-t-butyl acrylamide can also be used. When a polymer having (meth)acrylamide derivative is used, the polymer can be copolymerized with other copolymerizable monomers, as long as the polymer has a lower critical solution temperature. Particularly, in the present invention, polymers having at least one monomer selected from the group consisting of N-n-propyl acrylamide, N-isopropyl acrylamide, N-ethyl acrylamide, N,N-dimethylacrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine, and N-methacryloyl morpholine, or a copolymer of N-isopropyl acrylamide and N-t-butyl acrylamide are preferably used.

Polymers having an upper critical solution temperature used in the present invention include polymers having an upper critical solution temperature used in the present invention include polymers having at least one monomer selected from the group consisting of acryloyl glycineamide, acryloyl nipecotamide, acryloyl asparagineamide, and acryloyl glutamineamide, and the like. In addition, copolymers including at least two unlike monomers of these can be used as well. The abovementioned polymers can be copolymerized with other copolymerizable monomers such as acrylamide, acetyl acrylamide, biotinol acrylate, N-biotinyl-N'-methacryloyl trimethylene amide, acroyl sarcosineamide, methacryl sarcosineamide, acroyl methyluracil, etc. as long as the polymer has an upper critical solution temperature.

Additionally, in the present invention, a pH-responsive polymer which is able to aggregate and disperse by a change in pH can be used as the stimuli-responsive polymer. A pH at which a structural change of the pH-responsive polymer occurs is not limited to a particular pH; however, is preferably in the range of pH 4 to 10, more preferably in the range of pH 5 to 9, so as to avoid a deterioration of measurement/quantification accuracy due to denaturation of the first bound substance, second bound substance and the sample when the stimulus is applied.

The pH-responsive polymer includes polymers containing groups such as a carboxyl group, a phosphate group, a sulfonyl group, an amino group and the like as a functional group. More specifically, such pH-responsive polymer can be polymerized monomers having a dissociable group, including: (meth)acrylic acid; maleic acid; styrenesulfonic acid; 2-acrylamide-2-methylpropanesulfonic acid; phosphoryl ethyl (meth)acrylate; amino ethyl methacrylate; aminopropyl (meth)acrylamide; and dimethylaminopropyl(meth) acrylamide. In addition, such pH-responsive polymer can be the abovementioned monomers having a dissociable group copolymerized with other vinyl monomers, by the degree that does not deteriorate the pH response: (meth)acrylic esters such as methyl(meth)acrylate, ethyl(meth)acrylate and butyl (meth)acrylate; vinyl esters such as vinyl acetate and vinyl propionate; vinyl compounds such as styrene, vinyl chloride, N-vinylpyrrolidone; and (meth)acrylamides.

Particulate Magnetic Material

The particulate magnetic material used in the present invention can be constituted of a multivalent alcohol and magnetite. Any multivalent alcohol can be used without limitation, provided that it has at least two hydroxyl groups in constitutional units and can bind to an iron ion, for example, dextran, polyvinyl alcohol, mannitol, sorbitol, and cyclodextrin. For example, Japanese Unexamined Patent Application No. 2005-82538 discloses a method for manufacturing particulate magnetic material using dextran. Alternatively, a compound such as glycidyl methacrylate polymer, which has an epoxy group and forms a multivalent alcohol structure after ring opening, can be used as well. The mean particle size of the particulate magnetic material (magnetic particles) prepared using multivalent alcohol is preferably in the range of 0.9 nm to 1000 nm, in order to ensure superior dispersion. Particularly for increased detectability of the target substance, the mean particle size is preferably at least 2.9 nm and less than 200 nm.

Second Bound Substance

The second bound substance is a substance in which a hydrophilic second substance binds to a second affinity substance having affinity to the target substance.

Second Substance

The hydrophilic second substance is, for example, a water-soluble polymer such as: polymer containing, as a constitutional unit, polyoxyalkylene such as polyethylene glycol, polypropylene glycol, polyethylene oxide and polypropylene oxide; polymer containing an alcoholic hydroxyl group such as polyvinyl alcohol; and polyol such as water-soluble polysaccharides such as dextran, cyclodextrin, agarose and hydroxypropylcellulose. Such hydrophilic substances can have a functional group and the like in the polymer chain or at the end of the polymer chain to bind the second affinity substance.

First and Second Affinity Substances

The first affinity substance of the first bound substance and second affinity substance of the second bound substance are substances which can bind simultaneously to different sites of the target substance. For example, the first affinity substance and the second affinity substance may be a monoclonal antibody recognizing the different antigenic determinants of the target substance.

The antibody used herein can be any type of immunoglobulin molecule, for example an immunoglobulin molecule fragment which has an antigen binding site such as Fab and the antibody could be monoclonal or polyclonal, however preferably two different monoclonal antibodies recognizing two different antigenic sites of the target substance.

Preparation Method

A method for preparing the abovementioned kit is explained hereinafter.

Preparation of First Bound Substance

The first bound substance is prepared by binding the first substance and the first affinity substance. The binding method is not limited to a particular method; however, for example, substances having affinity to each other (e.g., avidin and biotin, glutathione and glutathione S-transferase) are bound to the first substance (for example, a stimuli-responsive polymer moiety) and to the first affinity substance (for example, the first antibody), and the first substance and the first affinity substance are bound to each other via these substances.

Specifically, as described in the International Publication Pamphlet No. WO 01/009141, biotin can be bound to the stimuli-responsive polymer by binding biotin or other affinity substances to a polymerizing functional group such as methacryl or acryl to produce an addition polymerizable monomer, which further copolymerizes with other monomers. In addition, avidin or other affinity substances can be bound to the first affinity substance by a commonly known method. Then, by mixing a biotin-bound stimuli-responsive polymer and an avidin-bound first affinity substance, the first affinity substance and the stimuli-responsive polymer are bound to each other via binding between avidin and biotin.

As an alternative, during polymerization, a monomer having functional groups such as a carboxyl group, an amino group or an epoxy group can be copolymerized with another monomer, then an antibody affinity substance (e.g., melon gel, protein A, protein G, etc.) can be bound to the polymer via the functional group according to a method known in the art. The antibody affinity substance thus obtained can be bound to the first antibody, to obtain a first bound substance in which the stimuli-responsive polymer binds to the first antibody of the target antigen.

Alternatively, during polymerization, a monomer having functional groups such as a carboxyl group, an amino group or an epoxy group can be copolymerized with another monomer, then the first antibody for the target antigen can be bound directly to these functional groups according to a commonly known method.

Alternatively, the first affinity substance and the stimuli-responsive polymer can be bound to the particulate magnetic material.

The first bound substance can be purified by subjecting the first substance containing the stimuli-responsive polymer to a condition where the stimuli-responsive polymer aggregates, followed by separating the aggregated polymer by centrifugation. The first bound substance can also be purified by binding the particulate magnetic material, and then the first affinity substance to the stimuli-responsive polymer, followed by collecting the magnetic material by applying a magnetic force.

The particulate magnetic material and the stimuli-responsive polymer can be bound by a method well-known in the art, such as a method of binding via a reactive functional group, or a method to graft polymerize from an active hydrogen in a multivalent alcohol or from a polymerizable unsaturated bond introduced to a multivalent alcohol itself in the magnetic substance (See, ADV. Polym. Sci., Vol. 4, p. 111, 1965; J. Polymer Sci., Part-A, 3, p 1031, 1965).

Next, a method for binding the hydrophilic second substance and the second antibody for the target antigen to produce a second bound substance will be described.

Preparation of Second Bound Substance

The second bound substance is prepared by binding directly or indirectly the second substance and the second affinity substance. The binding method is not limited to a particular method; however, for example, substances having affinity to each other (e.g., avidin and biotin, glutathione and glutathione S-transferase) are bound to both of the second substance and the second affinity substance (for example, the second antibody), and the second substance and the second affinity substance are indirectly bound to each other via the affinity substances.

When the second substance and the second affinity substance are directly bound, they can be bound via a functional group, for example, when using a functional group, maleimide-thiol coupling as in the method of Ghosh et al., (Ghosh et al.: Bioconjugate Chem., 1, 71-76, 1990) can be used.

The resulting kit can be used to detect or quantify the target substance, for example, in the following ways.

Detection Method

The detection method according to the present invention includes steps of: mixing a first bound substance, a second bound substance, and the sample; subjecting the mixture to conditions to aggregate the stimuli-responsive polymer, and determining if the stimuli-responsive polymer is dispersed or not. The steps will be described in detail hereinafter.

Mixing and Aggregation

To begin with, the first and the second bound substances are mixed, and then the sample is added thereto, to obtain a mixture. Next, this mixture is subjected to the conditions to aggregate the stimuli-responsive polymer. Then, if the target substance is present, aggregation of the stimuli-responsive polymer is inhibited by the hydrophilic moiety of the second bound substance and the stimuli-responsive polymer disperses. On the other hand, if the target substance is not present, the stimuli-responsive polymer aggregates since aggregation is not inhibited.

This phenomenon is explained with reference to FIGS. 1 and 2.

As shown in FIG. 1, a first bound substance 10 contains a stimuli-responsive polymer 11, and the stimuli-responsive polymer 11 is bound to a first antibody 13 for a target substance 50 via avidin 15 and biotin 17. Furthermore, the first bound substance 10 includes a particulate magnetic material 19, and the stimuli-responsive polymer 11 is bound to the surface of the magnetic material 19. On the other hand, a second bound substance 20 includes a hydrophilic second substance 21, and the second substance 21 is bound to a second antibody 23 for the target substance 50. Then, the first antibody 13 and the second antibody 23 can be bound simultaneously to different sites of the target substance 50.

Figure 2A:
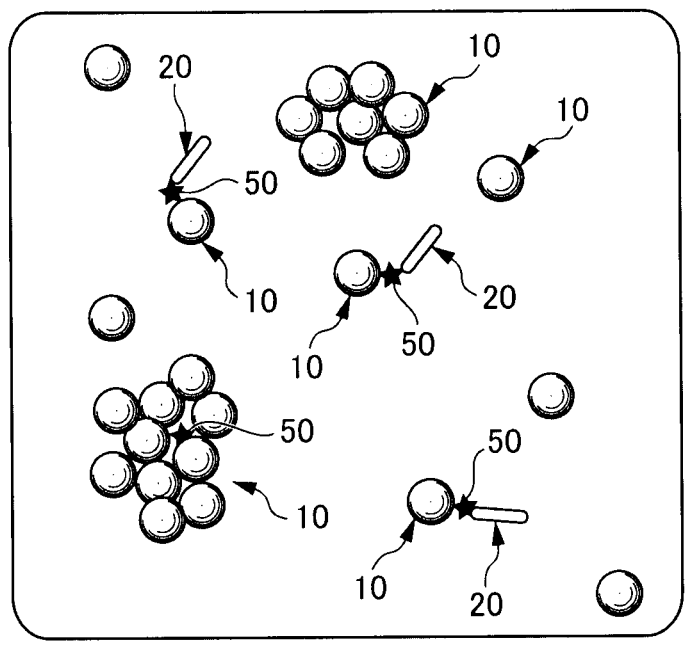
FIG. 2 is a schematic view showing a usage state of the bound substance according to the embodiment of the present invention.
Figure 2B:
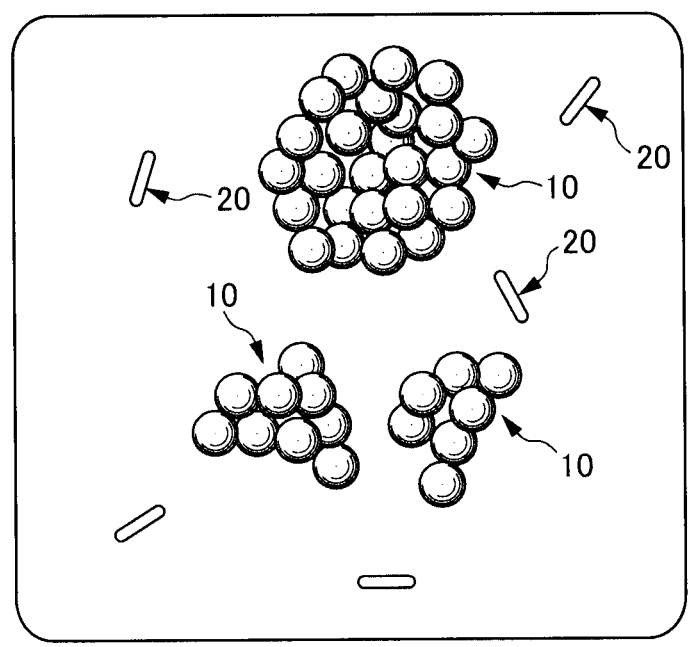

As shown FIG. 2, by subjecting a mixture of the first bound substance 10, the second substance 20, and the sample to predetermined conditions, in a case where the target substance is present, aggregation of the stimuli-responsive polymer is inhibited by the hydrophilic moiety of the second bound substance 20, and the stimuli-responsive polymer disperses (FIG. 2A). On the other hand, if the target substance 50 is not present, the stimuli-responsive polymer 11 aggregates since aggregation is not inhibited (FIG. 2B).

To aggregate the stimuli-responsive polymer 11, for example, in cases where a temperature-responsive polymer is used, a vessel containing the mixture can be moved to an incubator at an aggregation temperature of the temperature-responsive polymer. There are two types of temperature-responsive polymers: a polymer having an upper critical solution temperature (may hereinafter be abbreviated as UCST); and a polymer having a lower critical solution temperature (may hereinafter be abbreviated as LCST). For example, in cases where a polymer having a lower critical solution temperature with a LCST at 37° C. is used, the temperature-responsive polymer can be aggregated by placing the vessel containing the mixture in an incubator of no less than 37° C. Additionally, in cases where a polymer having an upper critical solution temperature with a UCST at 5° C. is used, the temperature-responsive polymer can be aggregated by placing the vessel containing the mixture in an incubator of no greater than 5° C.

In addition, in cases where a pH-responsive polymer is used, an acid solution or an alkaline solution can be added to the vessel containing the mixture. Specifically, to a vessel containing a dispersed mixture with a pH in the range in which a structural change of the pH-responsive polymer does not occur, an acid solution or an alkaline solution can be added to change the pH of the dispersed mixture to the range in which a structural change of the pH-responsive polymer occurs. For example, in cases where a pH-responsive polymer, which aggregates at a pH of no greater than 5 and disperses at a pH greater than 5, is used, an acid solution can be added to the vessel containing the mixture that is dispersed at a pH greater than 5, to lower the pH to be no greater than 5. Additionally, in cases where a pH-responsive polymer, which aggregates at a pH of no less than 10 and disperses at a pH of less than 10, is used, an alkaline solution can be added to the vessel containing the mixture that is dispersed at a pH less than 10, to raise the pH to be no less than 10. A pH at which a structural change of the pH-responsive polymer occurs is not limited to a particular pH; however, is preferably in the range of pH 4 to 10, more preferably in the range of pH 5 to 9.

Furthermore, in cases where a light-responsive polymer is used, the vessel containing the mixture can be irradiated with light having a wavelength that can aggregate the polymer. The preferred type of light depends on the type and structure of a light responsive functional group contained in the light-responsive polymer; however, generally ultraviolet radiation or visible radiation with a wavelength in the range of 190 to 800 nm can preferably be used. A luminous intensity thereof is preferably in the range of 0.1 to 1000 mW/cm$^2$. For improved measurement accuracy, the light-responsive polymer is preferably not dispersed, in other words is preferably aggregated, by the irradiation of light for the measurement of turbidity. In cases where a light-responsive polymer is used which disperses by the irradiation of light for the measurement of turbidity, for improved measurement accuracy, shortening irradiation time is preferred.

Note that the aggregation of the temperature-responsive polymer can take place after or simultaneously with binding of the first bound substance and the second bound substance to the target substance; however, the latter is preferred so as to shorten the processing time. However, if the conditions to aggregate the temperature-responsive polymer are greatly different from the conditions where the first bound substance and the second bound substance bind to a target substance, the former should be preferred.

The lower critical solution temperature is determined as follows. To begin with, a sample is added to a cell of an absorptiometer, and heated at a rate of 1° C./min. During this period, the change in transmittance at 550 nm is recorded. The transmittance is 100% when the polymer is dissolved to be transparent, and 0% when completely aggregated. LCST is defined by determining the temperature where the transmittance is 50%.

The upper critical solution temperature is determined as follows. A sample is cooled at a speed of 1° C./min, and the change in transmittance at 550 nm is recorded. The transmittance is 100% when the polymer is dissolved to be transparent, and 0% when completely aggregated. UCST is defined by determining the temperature where the transmittance is 50%.

Determination

The presence or absence of the dispersion can be confirmed, for example, visually or using turbidimetry. The turbidity can be calculated from the transmittance of a light scattering device. Low turbidity indicates that aggregation of the stimuli-responsive polymer is inhibited, and suggests the presence of the target substance. The wavelength of the light used in the present invention can be adjusted appropriately according to the particle size of the magnetic material, in order to obtain the desired detectability. The wavelength of the light is preferred to be in the range of visible light (e.g., 550 nm) so that conventional general-purpose devices can be used.

The visual observation or the turbidimetry measurement may be carried out intermittently at regular intervals, or continuously over time. Also, the determination can be performed based on the difference between the turbidity measured at a certain point in time and the turbidity measured at another point in time.

Quantitative Method

In a quantitative method according to the present invention, to begin with a first bound substance, a second bound substance and a sample are mixed, and the mixture thereof is subsequently subjected to predetermined conditions to aggregate the stimuli-responsive polymer. Then, turbidity of the mixture is measured, and the amount of a target substance in the sample is calculated based on a correlation equation between the amount of the target substance and the turbidity under the predetermined condition. An explanation is omitted for steps in the anterior half step of this method, which is similar to the aforementioned detection method.

Correlation Equation

The correlation equation between the amount of the target substance and the turbidity under the same condition as the abovementioned predetermined condition is constructed. The more data that is available on the amount of target substance and the turbidity constituting the correlation equation, the greater the reliability of the correlation equation becomes. Thus, the data should be based on at least 2 samples containing different amounts of the target substance, and preferably based on at least 3 samples containing different amounts thereof.

The correlation equation between the amount of the target substance and the turbidity is not limited to an equation indicating a direct correlation between the amount of the target substance and the turbidity, and can be a correlation equation between parameters reflecting the amount of the target substance and the turbidity.

Calculation

The amount of the target substance in a sample can be calculated by assigning the measured turbidity of the mixture to the resulting correlation equation.

Separation

In cases where the first substance contains a particulate magnetic material, the detection method or the quantitative method of the present invention preferably further includes a step of separating the aggregated magnetic material by applying a magnetic force. Thus, the aggregated magnetic material is separated from the foreign material including the magnetic material that is not aggregated. Therefore, the influence of the foreign material is excluded and the values measured such as the amount of separated magnetic material and the transmittance of light when the magnetic material is dispersed in a solvent reflect the presence of the target substance more consistently.

The application of a magnetic force can be performed by bringing a magnet close to the magnetic material. The magnetic force of the magnet depends on the magnitude of magnetic force of the magnetic material used. For example, a neodymium magnet by Magna Co., Ltd. can be used as the magnet.

The application of a magnetic force can be performed before or in parallel to the abovementioned determination; however, simultaneous parallel processing is preferred so that time for processing can be reduced. It is assumed that the turbidity of the mixture after separation should be relatively lower in the case of a mixture containing a foreign material, because the foreign material is entangled in the aggregated magnetic material and is also separated, when a magnetic force is applied.

It should be noted that the term "turbidimetry" in a detection method or a quantitative method includes not only measuring turbidity directly, but also measuring parameters reflecting turbidity. Such parameters include the difference of the turbidity measured at a plurality of points in time, the amount of the aggregated substance being separated, and the turbidity of the non-aggregated substance after separation. One of the plurality of points in time is preferably near the point where the turbidity is a maximum after applying a magnetic force to the negative control in which a target substance is not present. This result provides a larger difference in the measured turbidity from the other points in time, which allows for more accurate quantification of the target substance.

Target Substance

The target substance in a sample includes substances used for clinical diagnosis such as, human immunoglobulin G, M, A and E, human albumin, human fibrinogen (fibrin and degradation product thereof), α-fetoprotein (AFP), C-reactive protein (CRP), myoglobin, carcinoembryonic antigen, hepatitis virus antigen, human chorionic gonadotropin (hCG), human placental lactogen (HPL), HIV antigen, allergen, bacterial toxin, bacterial antigen, enzyme, hormone (for example, human thyroid stimulating hormone (TSH) and insulin), and drugs that are contained in body fluid, urine, sputum, stool and the like.

Exemplary Component and Usage of Kit

An exemplary component and usage of a kit for using in a method of the present invention are described below with an antigen as the target substance.

The reagent kit consists of the following reagents, for example,

The Antigen Detection Reagent Kit:

Reagent A: Particulate magnetic material to which a first antibody that binds specifically to the target antigen and a temperature-responsive polymer are bound Reagent B: A hydrophilic material in which a second antibody recognizes a site of the antigen different from the site recognized by the first antibody, and can bind to the target antigen simultaneously Reagent C: A standard sample of the substance to be measured (e.g., purified antigen)

Reagent D: A buffer for dilution (Buffer that can be used for dilution of the above reagent and the sample to be analyzed; for example, tris-chloride buffer or phosphate buffer)

In order to measure the turbidity, a conventional well-known device, which can maintain the vessel at the temperature to aggregate the polymer, and irradiate transmitted light of 200 to 900 nm, can be used.

The kit consisting of the above reagents can be used, for example, in the following method.

To begin with, 5 to 1000 μL of reagent A and 5 to 1000 μL of reagent B are mixed. To the solution containing the reagents A and B, (1) positive control containing a standard sample of the substance to be measured, (2) negative control with no target substance, (3) a sample having 5 to 1000 μL of a test solution are prepared to react at a temperature (for example about 0 to 30° C.) for a predetermined period. When a temperature-responsive polymer is used, each reaction mixture is added to a vessel kept at the aggregation temperature (e.g., 42° C.) of the polymer after the reaction. Then transmitted light of 550 nm is irradiated thereto to measure the turbidity in order to determine presence or absence of the antigen or to quantify the antigen.

In an alternative method, reagent A and the above (1), (2) and (3) are each reacted separately at a temperature at which the polymer disperses for a predetermined period and then, reagent B is added thereto. Or reagent B and the above (1), (2) and (3) are each reacted separately, and then reagent A is added thereto at the temperature at which the polymer disperses. The resulting mixture is left for a predetermined period for reaction. The reaction solution is added to a vessel kept at an aggregation temperature. Then transmitted light of 550 nm is irradiated thereto to measure the turbidity in order to determine the presence or absence of the antigen or to quantify the antigen.

EXAMPLES

Representative reagents used in Examples of the present invention are as follows: PBS buffer: commercially available PBS at a 10× concentration (81 mM Na2HPO4, 14.7 mM KH2PO4, 26.8 mM KCl, 1370 mM NaCl, pH 7.4, manufactured by Nippon Gene Co., Ltd.) was diluted to 1/10 (V/V) with purified water; Borate buffer solution: Borate buffer manufactured by Polysciences, Inc., 100 mM Boric acid, pH 8.5; and purified water: water purified by Direct-Q (trade name) manufactured by Millipore Corporation.

Example 1

In the present example, magnetic particles having surfaces thereof modified with biotin-bound temperature-responsive polymer, are used as the first bound substance, and biotin-bound polyvinyl alcohol is used as the second bound substance to detect and quantify streptavidin.

Preparation of First Bound Substance

Therma-Max LB Biotin (0.4 mass %) (manufactured by Magnabeat Inc.) was used as the magnetic particles having surfaces thereof modified with biotin-bound temperature-responsive polymer. 500 μL of Therma-Max LB Biotin was placed into a 1.5 mL microtube and heated to 42° C. to aggregate the Therma-Max LB Biotin. The aggregated substance was subsequently collected using a magnet, and the supernatant was removed. After removing the supernatant, 500 μL of PBS buffer (pH 7.4), including 0.5% (w/v) of BSA (manufactured by Sigma, Co.), 0.5% (w/v) of Tween (Registered Trademark) 20 and 10 mM EDTA, was added thereto and cooled to disperse. A dispersed solution of the first bound substance was thus obtained.

Preparation of Second Bound Substance

Preparation Example 1

Preparation Method of Biotin-Bound Polyvinyl Alcohol 1 mL of 1% (w/v) polyvinyl alcohol (M2O5, manufactured by Kuraray Co., Ltd., containing thiol group at one end) solution and 10 μL of 1% (w/v) Biotin-PEAC5-maleimide (manufactured by Dojindo Laboratories) solution were mixed and allowed to stand for one hour at 37° C. The reaction mixture was double purified using two spin columns (Microcon YM-10 manufactured by Millipore Corporation). Then purified water was added thereto bringing the total volume to 1 mL. 100 μL of the resulting solution was mixed with 900 μL of PBS buffer (pH 7.4), including 0.5% (w/v) of BSA (manufactured by Sigma, Co.), 0.5% (w/v) of Tween (Registered Trademark) 20 and 10 mM EDTA, to obtain a dispersed solution of the second bound substance.

Quantification of Streptavidin Using Magnetic Particles Having Surfaces Thereof Modified with Biotin-Bound Temperature-Responsive Polymer and Biotin-Bound Polyvinyl Alcohol Preparation of Sample Streptavidin (manufactured by Wako Pure Chemical Industries, Ltd.) was dissolved in purified water to obtain a 10 mg/mL solution. The solution was diluted to 13.3 μg/mL, 6.7 μg/mL, and 0 μg/mL with PBS buffer (pH 7.4) including 0.5% (w/v) of BSA (manufactured by Sigma, Co.), 0.5% (w/v) of Tween (Registered Trademark) 20 and 10 mM EDTA, and each was used as a sample.

Quantification

Figure 3:
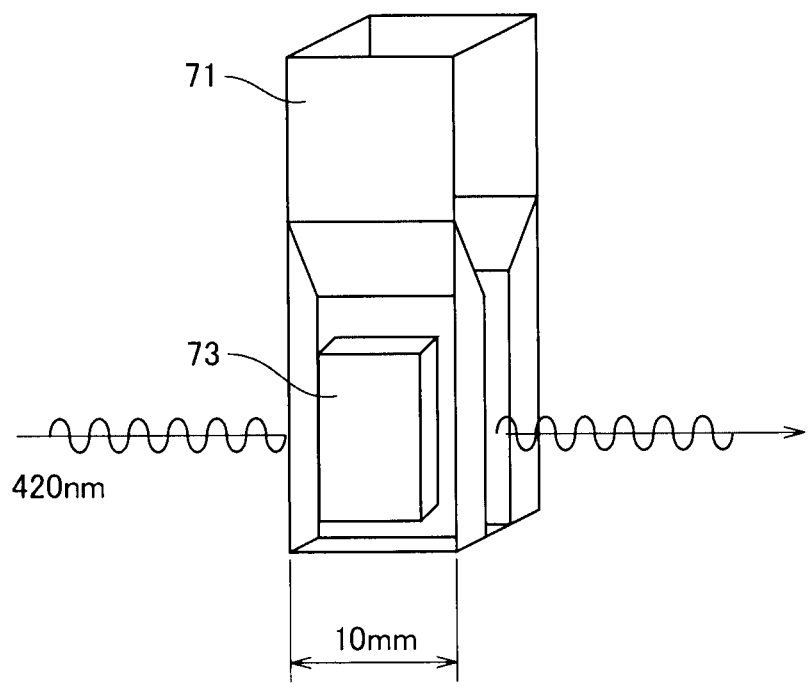
FIG. 3 is a diagram showing an aspect of application of magnetic force in a method according to an Example of the present invention.

As shown in FIG. 3, a neodymium permanent magnet 73 (manufactured by Seiko Sangyo Co., Ltd.) of 5 mm×9 mm×2 mm was attached outside the optical path of a semi-micro spectrophotometer cell 71. The cell 71 was installed in an ultraviolet-visible spectrophotometer V-660DS (manufactured by JASCO Corporation) provided with a cell temperature control unit, and held for at least 10 minutes at 37° C.

Figure 4:
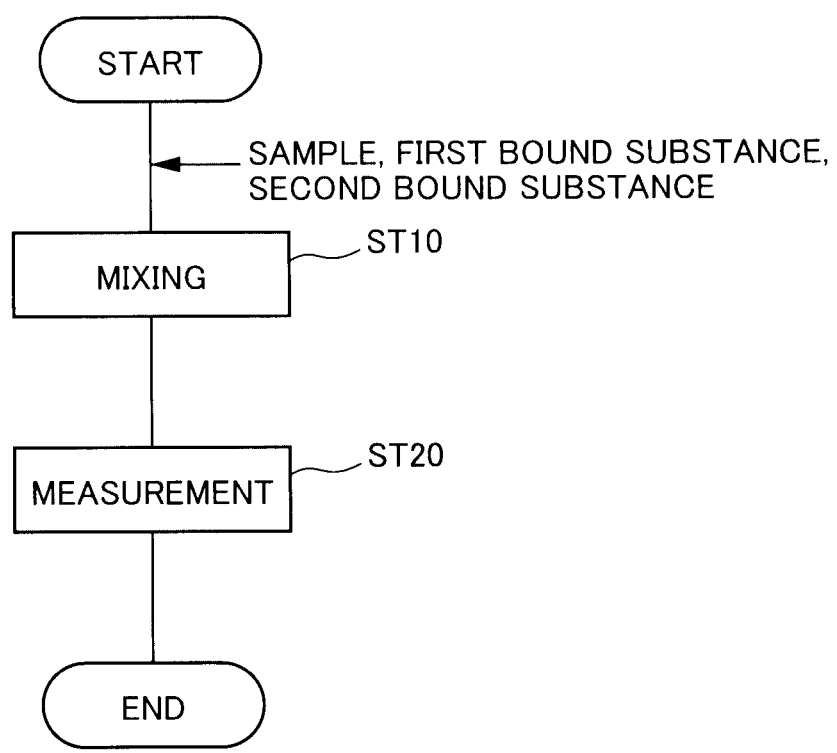
FIG. 4 is a flow chart of a method according to an Example of the present invention.

FIG. 4 is a flow chart of a quantitative method according to the present Example. The quantitative method includes steps of: mixing the abovementioned first bound substance, second bound substance and the sample (ST10); and determining the turbidity of the mixture (ST20).

Mixing

150 µL of the first bound substance, 120 µL of the second bound substance, and 750 µL of each sample were placed into microtubes, mixed by pipetting, and then agitated with a vortex mixer for 5 minutes.

Measurement of Turbidity

The agitated solution was dispensed into the cell 71, and after zeroing the spectrophotometer according to the instruction manual thereof, was immediately and continually measured for 1000 seconds, using a beam of light with a wavelength of 420 nm and a band width of 2.0 nm. The results are shown in FIG. 5.

Figure 5:
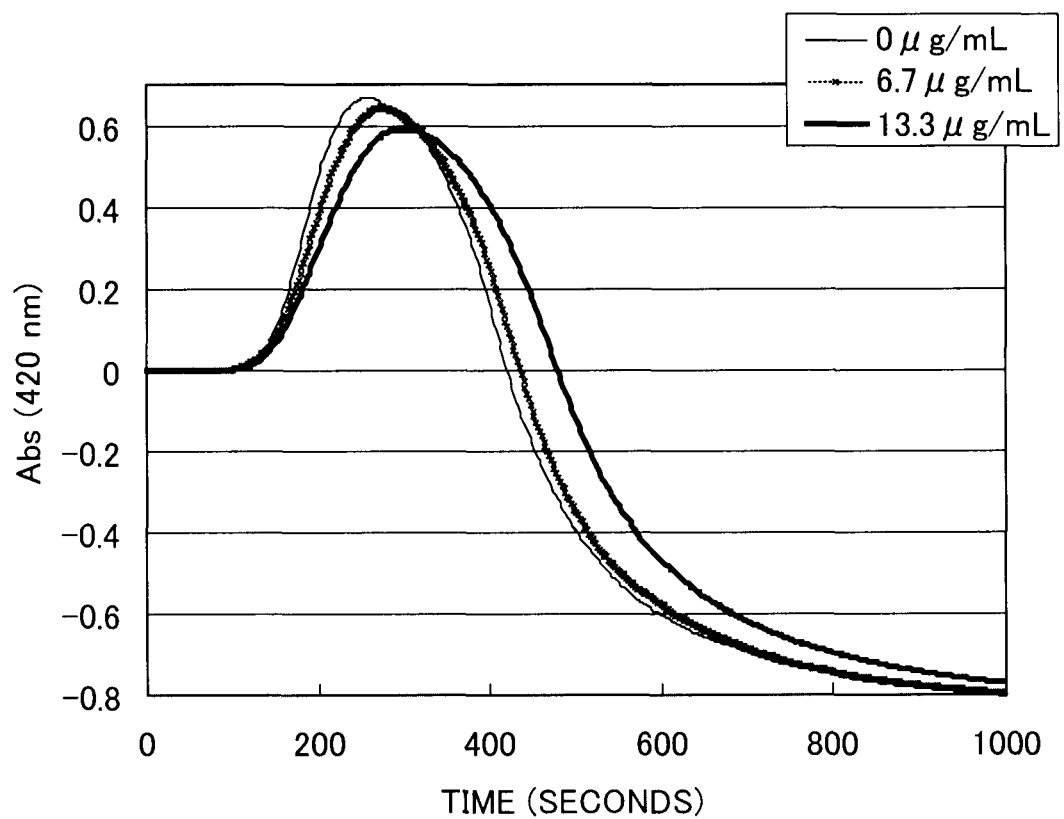
FIG. 5 is a graph showing a correlation between measurement time and turbidity in a method according to the Example of the present invention.

As shown in FIG. 5, until approximately 260 seconds, the greater the amount of streptavidin, the lower the turbidity. This is due to the temperature-responsive polymer being dispersed since aggregation thereof was inhibited as a result of being in the vicinity of the hydrophilic polyvinyl alcohol via streptavidin. However, the relation between the amount of streptavidin and the turbidity began to reverse from approximately 260 seconds, with the turbidity becoming less than the initial value as time progressed. It is assumed that this is due to the aggregated magnetic material being collected and separated by magnetic attraction.

Next, regarding each sample, the difference of the measured values between two points, taken at 260 seconds and 1000 seconds, was observed. The results are shown in Table 1.

TABLE 1

| Concentration of streptavidin (µg/mL) | Δ260-1000 |
|---|---|
| 13.3 | 1.32 |
| 6.7 | 1.43 |
| 0 | 1.47 |

As shown in Table 1, the difference of the measured values between 260 seconds and 1000 seconds depended on the amount of streptavidin. In other words, as the concentration of streptavidin increased the difference between the measured value at 260 seconds and 1000 seconds decreased. Thus, measuring the difference between the measured values at 260 seconds and 1000 seconds allows for the detection or quantification of the target substance.

Figure 8:
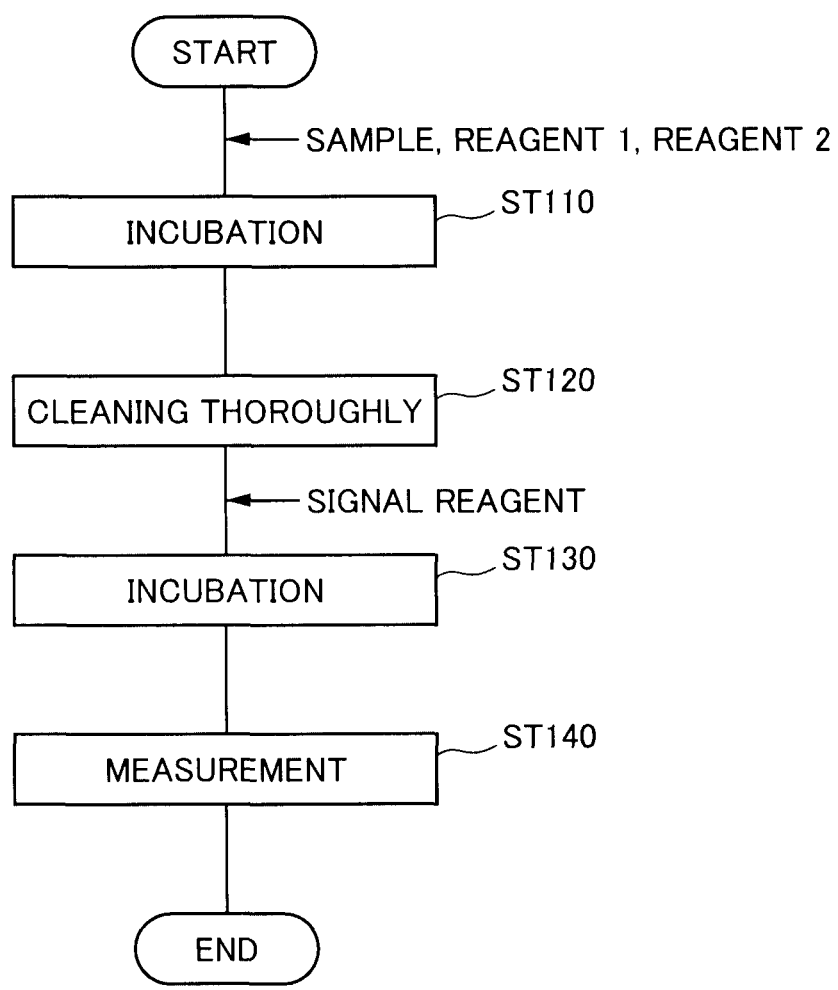
FIG. 8 is a flow chart of a method according to the conventional art.

The time for detection which was 1000 seconds was much shorter than conventional systems, which require approximately 90 minutes including incubation time (see FIG. 8). Furthermore, the target substance can be detected or quantified conveniently by only conducting ST10 and ST20 operations (see FIG. 4) on the actual sample.

The abovementioned results showed that the turbidity changes according to the concentration of streptavidin; in other words, the concentration of streptavidin can be determined by measuring the turbidity. Therefore, it was confirmed that the method according to the present invention is a novel method not requiring any special reagent or instrument such as a secondary antibody, luminescent reagent or photodetector, and allowing for quick, inexpensive and convenient detection and quantification of a target substance.

Example 2

The present Example exemplifies detection and quantification of glutathione (GSH) by using magnetic particles having surfaces thereof modified with temperature-responsive polymer including a protected thiol group (hereinafter also referred to as TM-LPDP) as the first bound substance, and N-hydroxysuccinimide-bound polyethylene glycol (hereinafter also referred to as NHS-PEG) SUN BRIGHT ME-400CS (manufactured by NOF CORPORATION, with average molecular weight 40000) as the second bound substance.

Preparation of First Bound Substance

Therma-Max LAm Amine (0.4 mass %) manufactured by Magnabeat Inc. (hereinafter referred to as TM-LAm) was used as the magnetic particles having surfaces thereof modified with amino group-bound temperature-responsive polymer. 2 mL of TM-LAm was placed into a 2 mL microtube and heated to 42° C. to aggregate the TM-LAm. The aggregated substance was subsequently collected using a magnet, and the supernatant was removed. After removing the supernatant, 2 mL of borate buffer solution was added thereto to substitute the solvent thereof and sufficiently disperse TM-LAm. Borate buffer solution containing magnetic particles was thus obtained.

Subsequently, 2 mg of N-succinimidyl-3-(2-pyridyldithio) propionate (manufactured by Dojindo Laboratories, SPDP) dissolved in 100 µL of dimethyl sulfoxide was mixed with the borate buffer solution containing magnetic particles, and agitated overnight at 20° C. The agitated liquid was heated to 42° C. The aggregated substance was subsequently collected using a magnet, and the supernatant was removed. After removing the supernatant, 2 mL of PBS buffer was added to sufficiently disperse the aggregated substance. The abovementioned washing was repeated twice, thereby removing unreacted SPDP. The dispersed liquid was heated to 42° C., the aggregated substance was collected using a magnet, and the supernatant was removed. Thereafter, the magnetic particles having surfaces thereof modified with temperature-responsive polymer including a protected thiol group was dispersed in PBS buffer, thereby preparing the first bound substance (particle content: 0.3 mass %).

Quantification of Glutathione Using Magnetic Particles Having Surfaces Thereof Modified with Temperature-Responsive Polymer Including a Protected Thiol Group and N-Hydroxysuccinimide-Bound Polyethylene Glycol Preparation of Sample Reduced glutathione (manufactured by Wako Pure Chemical Industries, Ltd.) was dissolved in 1 mL of PBS buffer containing 10 mM EDTA. The solution was diluted to 12 µg/mL, 6 µg/mL, and 3 µg/mL with PBS buffer including 10 mM EDTA, and a sample not containing glutathione was prepared, and each was used as a sample.

Quantification

Mixing

500 µL of the above first bound substance dispersed in PBS buffer was placed into a 1.5 mL tube and 10 µL of 0.5 M EDTA solution (pH 8, manufactured by Nippon Gene Co., Ltd.) was added thereto and mixed, thereby preparing a solution. 200 µL of the above sample was added thereto and agitated for 6 hours at 4° C. Then 700 µL (200 µM) of NHS-PEG was added into the tube and agitated for 12 hours at 4° C. Thereafter, 800 µL of PBS was added to 400 µL of the agitated substance, thereby obtaining a mixture.

Derivation of Correlation Equation

The mixture was dispensed into the cell 71 used in Example 1, and turbidity thereof was measured in the same condition as that of Example 1. The results are shown in FIG. 6.

Figure 6:
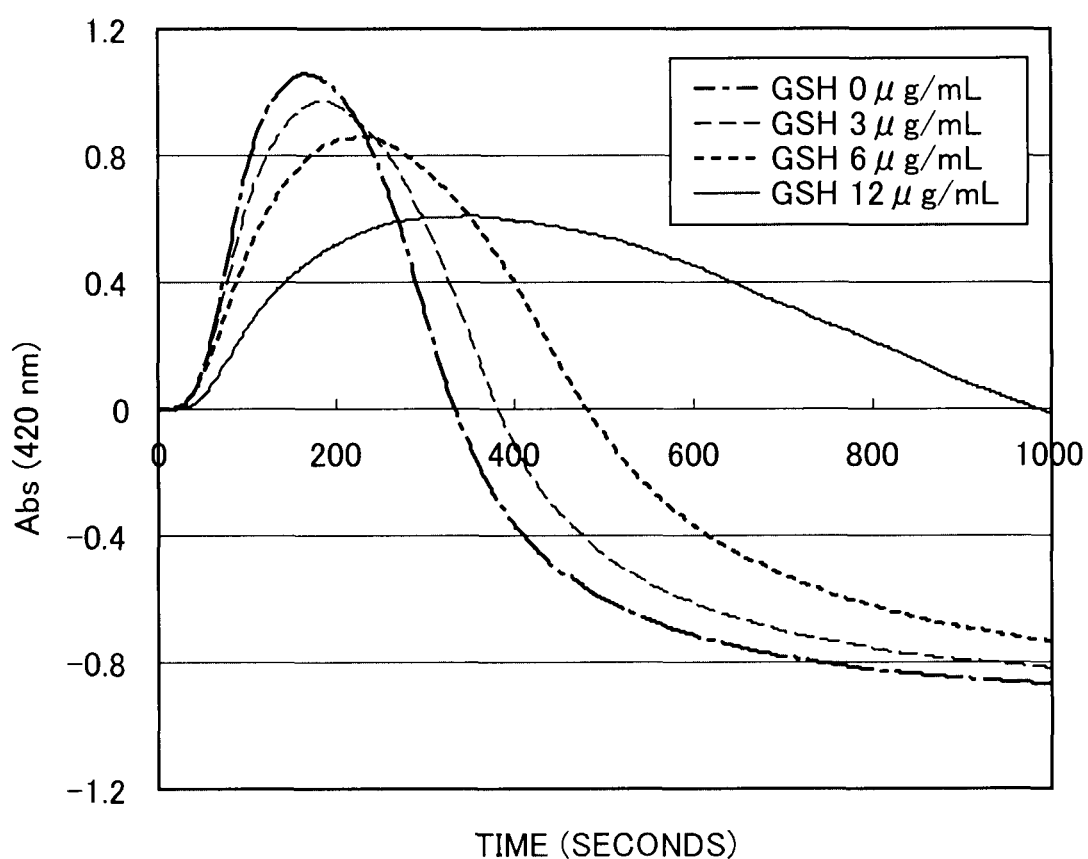
FIG. 6 is a graph showing a correlation between measurement time and turbidity in a method according to another Example of the present invention.

As shown in FIG. 6, there is already a large difference in turbidity between the samples from 50 seconds after starting measurement. This shows that very rapid detection and quantification of a target substance in a sample is possible. In addition, it was confirmed that a measurement point is preferably set at 450 seconds after starting measurement, since the difference in turbidity between the samples was the greatest at 450 seconds after starting measurement.

The first bound substance, the second bound substance and the samples were stored in the dark at 4° C. and turbidity thereof was measured in the same procedure once a day for three days. The results are shown in Table 2. It should be noted that the values shown in Table 2 are averages of the values obtained by subtracting the turbidity of the samples at 450 seconds after starting measurement from the turbidity at the beginning of the measurement ($\Delta$ 0-450).

TABLE 2

| GSH (μg/mL) | $\Delta$ 0-450 | | |
| --- | --- | --- | --- |
| | Average | CV (%) | STDEVA |
| 0 | −0.51 | 2.8 | 0.014 |
| 3 | −0.33 | 3.3 | 0.011 |
| 6 | 0.14 | 2.2 | 0.003 |
| 12 | 0.57 | 0.2 | 0.001 |

As shown in Table 2, CV (coefficient of variance) was no greater than 3.3, which was very low, in all measurement points for 3 days. Therefore, it was confirmed that, according to the system of the present example, high reproducibility can be obtained. Herein, the CV (%) was calculated in accordance with an equation CV=Standard Deviation (STDEVA)/Average×100.

Figure 7:
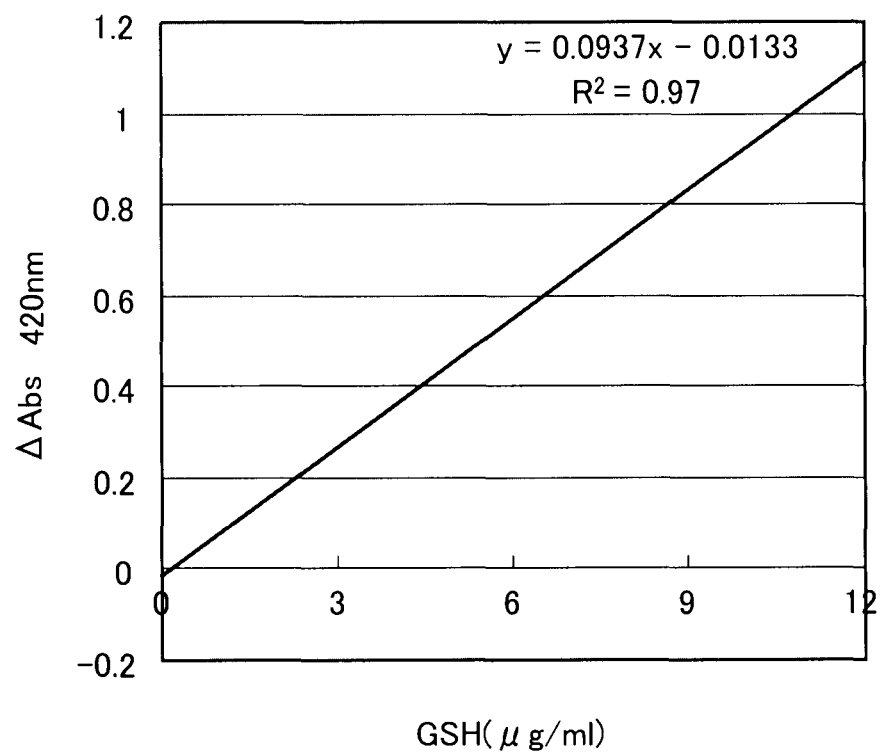
FIG. 7 is a graph showing a correlation between amount of a target substance and turbidity in a method according to the Example of FIG. 6.

In addition, FIG. 7 is a graph showing the correlation between the amount of glutathione and the value obtained by calculating the difference between the average of values obtained by subtracting the turbidity of each sample at 450 seconds after starting measurement and the turbidity thereof at the beginning of the measurement (GSH 3 μg/ml, 6 μg/ml, 12 μg/ml, $\Delta$ 0-450), from an average of values obtained by subtracting the turbidity of each sample containing 0 μg of glutathione at 450 seconds after starting measurement from the turbidity thereof at the beginning of the measurement (GSH 0 μg/ml, $\Delta$ 0-450).

As shown in FIG. 7, the correlation equation obtained was y=0.0937x−0.0133 (wherein x is amount of glutathione and y is the turbidity). In addition, correlation coefficient $R^2$ was 0.97, which is extremely high, and thus it was confirmed that the amount of glutathione can be quantified with a high degree of accuracy by this correlation equation. This shows that, as in the present example, quantification of ultra-high accuracy of a target substance in a sample is possible by using, as the second substance, a polyoxyalkylene which is not readily nonspecifically adsorbed by biological substances, such as polyethylene glycol which causes steric repulsion when it is at the vicinity of the particle surface. Polyol also is expected to have a similar effect.

The present invention is not limited to the above described embodiments. Accordingly, variations, improvements, and other modifications are included in the scope of the present invention without departing from the spirit or scope of the present invention. Although a stimuli-responsive polymer is necessarily used in the present invention, the invention is not limited to polymers, and a stimuli-responsive low-molecular-weight compound can also be used. Such a low molecular-weight compound includes those disclosed in Japanese Patent Publication No. 3693979, Japanese Patent Publication No. 3916330, Japanese Unexamined Patent Application Publication No. 2002-85957, Japanese Patent Publication No. 4071738, Japanese Patent Publication No. 2869684, Japanese Patent Publication No. 2927601, Japanese Patent Publication No. 3845249, Japanese Unexamined Patent Application Publication No. 2006-242597, and the like.

What is claimed is:

1. A method for detecting a target substance in a sample, comprising steps of:
    mixing a first bound substance in which a first substance containing a stimuli-responsive polymer binds to a first affinity substance having affinity to the target substance, a second bound substance in which a hydrophilic second substance binds to a second affinity substance having affinity to the target substance, and the sample; placing the mixture under conditions to aggregate the stimuli-responsive polymer; and determining if the stimuli-responsive polymer is dispersed or not, wherein
    the first affinity substance and the second affinity substance can simultaneously bind to different sites of the target substance; and determining that the target substance is present in a case in which aggregation inhibition of the stimuli-responsive polymer is confirmed via inhibition of the aggregation of the stimuli-responsive polymer by the second bound substance, and that the target substance is not present in a case in which aggregation inhibition of the stimuli-responsive polymer is not confirmed; wherein the step of determining if dispersion is present or not is carried out under conditions to aggregate the stimuli-responsive polymer.

2. The method according to claim 1, wherein the first substance contains a particulate magnetic material, and
    the method further comprises a step of separating aggregated magnetic material by applying a magnetic force.

3. A method for quantifying a target substance in a sample, comprising steps of:
    mixing a first bound substance in which a first substance containing a stimuli-responsive polymer binds to a first affinity substance having affinity to the target substance, a second bound substance in which a hydrophilic second substance binds to a second affinity substance having affinity to the target substance, and the sample; placing the mixture under predetermined conditions to aggregate the stimuli-responsive polymer; measuring a change in the turbidity of the mixture via inhibition of the aggregation of the stimuli-responsive polymer by the second bound substance; and
    calculating the amount of the target substance in the sample based on a correlation equation between the amount of the target substance and the turbidity under the predetermined condition, wherein the step of measuring the turbidity is carried out under conditions to aggregate the stimuli-responsive polymer.

4. The method according to claim 3, wherein the first substance contains a particulate magnetic material, and
    the method further comprises a step of separating aggregated magnetic material by applying a magnetic force.

* * * * *